(12) United States Patent
Scheel-Krüger et al.

(10) Patent No.: US 7,381,733 B2
(45) Date of Patent: Jun. 3, 2008

(54) TROPANE DERIVATIVES HAVING DOPAMINE REUPTAKE INHIBITOR ACTIVITY FOR THE TREATMENT OF ISCHEMIC DISEASES

(75) Inventors: Jørgen Scheel-Krüger, Ballerup (DK); Lars Christian B. Rønn, Ballerup (DK)

(73) Assignee: Neurosearch A/S, Ballerup (DK)

( * ) Notice: Subject to any disclaimer, the term of this patent is extended or adjusted under 35 U.S.C. 154(b) by 396 days.

(21) Appl. No.: 10/494,922

(22) PCT Filed: Nov. 28, 2002

(86) PCT No.: PCT/DK02/00796

§ 371 (c)(1), (2), (4) Date: Jun. 15, 2004

(87) PCT Pub. No.: WO03/045388

PCT Pub. Date: Jun. 5, 2003

(65) Prior Publication Data

US 2005/0020621 A1 Jan. 27, 2005

(30) Foreign Application Priority Data

Nov. 30, 2001 (DK) ............................. 2001 01781

(51) Int. Cl.
*A01N 43/42* (2006.01)
*A61K 31/44* (2006.01)
*C07D 451/02* (2006.01)
*C07D 401/00* (2006.01)
*C07D 405/00* (2006.01)

(52) U.S. Cl. ................. 514/304; 546/124; 546/125; 546/126; 546/132

(58) Field of Classification Search ............... 546/124, 546/125, 126, 132; 514/304
See application file for complete search history.

(56) References Cited

U.S. PATENT DOCUMENTS

| 4,179,567 A | 12/1979 | Clarke et al. |
| 5,128,118 A * | 7/1992 | Carroll et al. ............. 424/1.85 |
| 5,272,160 A | 12/1993 | Chenard |
| 5,444,070 A | 8/1995 | Moldt et al. |
| 5,980,860 A * | 11/1999 | Kung et al. ................ 424/1.65 |

FOREIGN PATENT DOCUMENTS

| EP | 0 604 352 A2 | 6/1994 |
| EP | 0 604 352 A3 | 6/1994 |
| EP | 0 604 354 A2 | 6/1994 |
| EP | 0 604 355 A2 | 6/1994 |
| WO | WO 95/28401 A | 10/1995 |
| WO | WO 96/06081 A | 2/1996 |
| WO | WO 97/16451 A | 5/1997 |
| WO | WO 97/30997 A | 8/1997 |
| WO | 9961023 | * 12/1999 |
| WO | WO 01/28550 A | 4/2001 |
| WO | WO 02/064128 A | 8/2002 |

OTHER PUBLICATIONS

Schmetterer et al., Clinical pharmacology and therapeutics, "Effects of antiglaucoma drugs on ocular hemodynamics in healthy volunteers", 1997, vol. 61, pp. 583-595.*
Holmang et al., Diabetes, "Induced of insulin resistance by glucosamine reduces blood flow but not interstitial levels of either glucose or insulin", 1999, vol. 48, pp. 106-111.*
Smith et al., Tetrahedron Letters, "The synthesis of tricyclic cocaine analogs via the 1,3-Dipolar cycloaddition of oxidopyridinium betaines", 1998, vol. 39, pp. 197-200.*
Smith et al., J. Am. Chem. Soc., "Tuning the selectivity of monoamine transporter inhibitors by the stereochemistry of the nitrogen lone pair", 1998, vol. 120, pp. 9072-9073.*
Akiyama et al., Brain Research, vol. 561, pp. 120-127.*
Du et al., Journal of Cardiovascular Pharmacology, "Protection of Neuronal Uptake-1 Inhibitors in Ischemic and Anoxic Hearts BY Norepinephrine-Dependent and -Independent Mechanisms", 1998, pp. 621-628.
Neurochemistry International, V. Leviel, "The reverse transport of DA, what physiological significance?", England, vol. 38, No. 2, Feb. 2001, pp. 83-106.

* cited by examiner

*Primary Examiner*—Margaret D. Seaman
*Assistant Examiner*—Niloofar Rahmani
(74) *Attorney, Agent, or Firm*—Birch, Stewart, Kolasch & Birch, LLP

(57) ABSTRACT

The present invention relates to the use of tropane derivatives having dopamine reuptake inhibitor activity for the treatment of diseases associated with reduced blood flow to the brain or with instances of a temporary break in blood supply to the brain, such as ischemic diseases.

8 Claims, No Drawings

TROPANE DERIVATIVES HAVING DOPAMINE REUPTAKE INHIBITOR ACTIVITY FOR THE TREATMENT OF ISCHEMIC DISEASES

TECHNICAL FIELD

The present invention relates to the use of tropane derivatives having dopamine reuptake inhibitor activity for the treatment of diseases associated with reduced blood flow to the brain or with instances of a temporary break in blood supply to the brain, such as ischemic diseases.

BACKGROUND ART

Cerebral ischemia can result in varying degrees of tissue damage. Conditions of severe ischemia can produce irreversible injury, whereas in conditions of moderate ischemia, tissue damage may be reversible. The reversibility of tissue damage—i.a. in the striatum—is important for the development of new therapeutic approaches for treatment.

In connection with an incidence of cerebral ischemia, an excessive amount of glutamate is released from the cortex to the striatum resulting in an excessive depolarization of dopaminergic nerve terminals primarily mediated by sodium influx. This depolarization results in a massive efflux of dopamine, which in turn exerts a neurodegenerative effect in the striatum.

Compounds capable of reducing the striatal dopamine level in such situations would therefore be considered useful for the treatment treatment of diseases associated with reduced blood flow to the brain or with instances of a temporary break in blood supply to the brain, such as ischemic diseases.

It has been mentioned that dopamine release mediated by reversal of the dopamine transporter (DAT) may also be of importance in ischemic conditions in the striatum such that a part of the neurodegenerative changes in the striatum following ischemia results from dopamine release mediated by the dopamine transporter (Leviel V, Neurochemistry International, 38, 83-106, 2001).

DETAILED DISCLOSURE OF THE INVENTION

It has now been found that a tropane derivative having dopamine reuptake inhibitor activity is useful in the treatment, prevention or alleviation of a disease associated with reduced blood flow to the brain or with an instance of a temporary break in blood supply to the brain.

Thus, in a first aspect the invention provides the use of a tropane derivative having dopamine reuptake inhibitor activity or a pharmaceutically acceptable salt thereof for the manufacture of a medicament for the treatment, prevention or alleviation of a disease associated with reduced blood flow to the brain or with an instance of a temporary break in blood supply to the brain.

In a second aspect, the invention provides a method for the treatment, prevention or alleviation of a disease associated with reduced blood to the brain or with an instance of a temporary break in blood supply to the brain in a subject, comprising administering to said subject a therapeutically effective amount of a tropane derivative having dopamine reuptake inhibitor activity or a pharmaceutically acceptable salt thereof.

In one embodiment, the tropane derivative having dopamine reuptake inhibitor activity is a compound of the general formula (I)

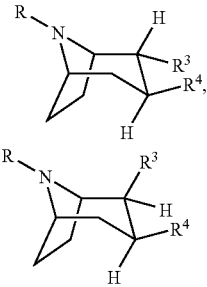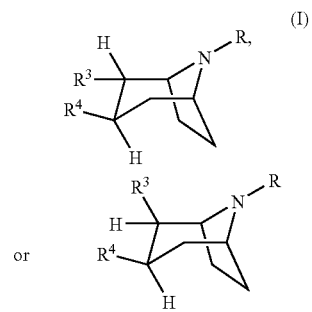

or a pharmaceutically acceptable addition salt thereof or the N-oxide thereof, wherein R is hydrogen, alkyl, alkenyl, alkynyl, cycloalkyl, cycloalkylalkyl or 2-hydroxyethyl;

$R^3$ is $CH_2$—X—R', wherein X is O, S, or NR";

wherein R" is hydrogen or alkyl; and

R' is alkyl, alkenyl, alkynyl, cycloalkyl, cycloalkylalkyl, or —CO-alkyl;

heteroaryl which may be substituted one or more times with alkyl, cycloalkyl, or cycloalkylalkyl;

phenyl which may be substituted one or more times with substituents selected from the group consisting of halogen, $CF_3$, CN, alkoxy, alkyl, alkenyl, alkynyl, amino, nitro, and heteroaryl;

phenylphenyl;

pyridyl which may be substituted one or more times with substituents selected from the group consisting of halogen, $CF_3$, CN, alkoxy, alkyl, alkenyl, alkynyl, amino, nitro, and heteroaryl;

thienyl which may be substituted one or more times with substituents selected from the group consisting of halogen, $CF_3$, CN, alkoxy, alkyl, alkenyl, alkynyl, amino, nitro, and heteroaryl; or benzyl which may be substituted one or more times with substituents selected from the group consisting of halogen, $CF_3$, CN, alkoxy, alkyl, alkenyl, alkynyl, amino, nitro, and heteroaryl; or $(CH_2)_n CO_2 R^{11}$, $COR^{11}$, or $CH_2 R^{12}$;

wherein $R^{11}$ is alkyl, cycloalkyl, or cycloalkylalkyl;

phenyl which may be substituted one or more times with substituents selected from the group consisting of halogen, $CF_3$, CN, alkoxy, alkyl, alkenyl, alkynyl, amino, nitro, and heteroaryl;

phenylphenyl;

pyridyl which may be substituted one or more times with substituents selected from the group consisting of halogen, $CF_3$, CN, alkoxy, alkyl, alkenyl, alkynyl, amino, nitro, and heteroaryl;

thienyl which may be substituted one or more times with substituents selected from the group consisting of halogen, $CF_3$, CN, alkoxy, alkyl, alkenyl, alkynyl, amino, nitro, and heteroaryl; or benzyl;

n is 0 or 1; and
R$^{12}$ is
  O-phenyl which may be substituted one or more times with substituents selected from the group consisting of halogen, CF$_3$, CN, alkoxy, alkyl, alkenyl, alkynyl, amino, nitro, and heteroaryl; or
  O—CO-phenyl which may be substituted one or more times with substituents selected from the group consisting of halogen, CF$_3$, CN, alkoxy, alkyl, alkenyl, alkynyl, amino, nitro, and heteroaryl; or
CH=NOR';
wherein R' is
  hydrogen;
  alkyl, cycloalkyl, cycloalkylalkyl, alkenyl, alkynyl or aryl; all of which may be substituted with
    —COOH;
    —COO-alkyl;
    —COO-cycloalkyl; or
    phenyl which may be substituted one or more times with substituents selected from the group consisting of halogen, CF$_3$, CN, alkyl, cycloalkyl, alkoxy, cycloalkoxy, alkenyl, alkynyl, amino, and nitro;
R$^4$ is
3,4-methylenedioxyphenyl or
phenyl, benzyl, naphthyl, or heteroaryl all of which may be substituted one or more times with substituents selected from the group consisting of halogen, CF$_3$, CN, alkoxy, cycloalkoxy, alkyl, cycloalkyl, alkenyl, alkynyl, amino, nitro, and heteroaryl.

In a special embodiment of the compound of general formula I, R$^3$ is
1,2,4-oxadiazol-3-yl which may by substituted in the 5 position with
  alkyl, cycloalkyl, or cycloalkylalkyl;
  phenyl which may be substituted one or more times with substituents selected from the group consisting of halogen, CF$_3$, CN, alkoxy, alkyl, alkenyl, alkynyl, amino, nitro, and heteroaryl;
  phenylphenyl; or
  benzyl which may be substituted one or more times with substituents selected from the group consisting of halogen, CF$_3$, CN, alkoxy, alkyl, alkenyl, alkynyl, amino, nitro, and heteroaryl; or
1,2,4-oxadiazol-5-yl which may by substituted in the 3 position with
  alkyl, cycloalkyl, or cycloalkylalkyl;
  phenyl which may be substituted one or more times with substituents selected from the group consisting of halogen, CF$_3$, CN, alkoxy, alkyl, alkenyl, alkynyl, amino, nitro, and heteroaryl;
  phenylphenyl;
  benzyl which may be substituted one or more times with substituents selected from the group consisting of halogen, CF$_3$, CN, alkoxy, alkyl, alkenyl, alkynyl, amino, nitro, and heteroaryl;
  pyridyl which may be substituted one or more times with substituents selected from the group consisting of halogen, CF$_3$, CN, alkoxy, alkyl, alkenyl, alkynyl, amino, nitro and heteroaryl; or
  thienyl which may be substituted one or more times with substituents selected from the group consisting of halogen, CF$_3$, CN, alkoxy, alkyl, alkenyl, alkynyl, amino, nitro and heteroaryl.

In a further special embodiment of the compound of general formula I, R$^3$ is
CH$_2$—X—R',
wherein X is O, S, or NR'';
wherein R'' is hydrogen or alkyl; and
R' is alkyl, alkenyl, alkynyl, cycloalkyl, cycloalkylalkyl, or —CO-alkyl.

In a still further embodiment of the compound of general formula I, R3 is
CH=NOR';
wherein R' is
  hydrogen;
  alkyl, cycloalkyl, cycloalkylalkyl, alkenyl, alkynyl or aryl; all of which may be substituted with
    —COOH;
    —COO-alkyl;
    —COO-cycloalkyl; or
    phenyl which may be substituted one or more times with substituents selected from the group consisting of halogen, CF$_3$, CN, alkyl, cycloalkyl, alkoxy, cycloalkoxy, alkenyl, alkynyl, amino, and nitro.

In a further special embodiment of the compound of general formula I, R$^4$ is phenyl, which is substituted once or twice with substituents selected from the group consisting of halogen, CF$_3$, CN, alkoxy, cycloalkoxy, alkyl, cycloalkyl, alkenyl, alkynyl, amino, nitro, and heteroaryl.

In a more special embodiment, R$^4$ is phenyl substituted once or twice with chlorine.

In a further special embodiment, the tropane derivative having dopamine reuptake inhibitor activity is a (1R,2R,3S)-2,3-disubstituted tropane derivative of formula I.

In a still further embodiment, the tropane derivative having dopamine reuptake inhibitory activity is a compound of general formula I wherein
R$^3$ is
  —CH$_2$—X—R', wherein X is O or S, and R' is methyl, ethyl, propyl, or cyclopropylmethyl;
  CH=NOR';
  wherein R' is hydrogen or alkyl, or
  1,2,4-oxadiazol-5-yl which may by substituted in the 3 position with alkyl.

In a still further embodiment, the tropane derivative having dopamine reuptake inhibitory activity is a compound of general formula I wherein R is hydrogen, methyl, ethyl or propyl.

In a still further embodiment, the tropane derivative having dopamine reuptake inhibitory activity is a compound of general formula I wherein R$^4$ is 3,4-dichlorophenyl.

In a special embodiment, the tropane derivative having dopamine reuptake inhibitor activity is a compound of the general formula (I) selected from:
(1R,2R,3S)-2-(3-Cyclopropyl-1,2,4-oxadiazol-5-yl)-3-(4-fluorophenyl)tropane;
(1R,2R,3S)-2-(3-Phenyl-1,2,4-oxadiazol-5-yl)-3-(4-fluorophenyl)tropane;
(1R,2R,3S)-2-(3-Phenyl-1,2,4-oxadiazol-5-yl)-3-(4-methylphenyl)-tropane;
(1R,2R,3S)-2-(3-Benzyl-1,2,4-oxadiazol-5-yl)-3-(4-fluorophenyl)tropane;
(1R,2R,3S)-2-(3-(4-Phenyl-phenyl)-1,2,4-oxadiazol-5-yl)-3-(4-fluorophenyl)tropane;
(1R,2R,3S)-2-(3-Phenyl-1,2,4-oxadiazol-5-yl)-3-(2-naphthyl)tropane;
(1R,2R,3S)-3-(3,4-Dichlorophenyl)tropane-2-aldoxime;
(1R,2R,3S)-3-(3,4-Dichlorophenyl)-tropane-2-O-methyl-aldoxime;

(1R,2R,3S)-3-(3,4-Dichlorophenyl)tropane-2-O-benzyl-aldoxime;
(1R,2R,3S)-3-(3,4-Dichlorophenyl)tropane-2-O-ethoxycarbonylmethyl-aldoxime;
(1R,2R,3S)-3-(3,4-Dichlorophenyl)tropane-2-O-methoxycarbonylmethyl-aldoxime;
(1R,2R,3S)-3-(3,4-Dichlorophenyl)tropane-2-O-(1-ethoxycarbonyl-1,1-dimethyl-methyl)-aldoxime;
(1R,2R,3S)-3-(3,4-Dichlorophenyl)tropane-2-O-carboxymethyl-2-aldoxime;
(1R,2R,3S)-N-Normethyl-3-(3,4-dichlorophenyl)tropane-2-O-methyl-aldoxime;
(1R,2R,3S)-N-Normethyl-3-(3,4-dichlorophenyl)tropane-2-O-benzyl-aldoxime;
(1R,2R,3S)-3-(4-Methylphenyl)tropane-2-O-methyl-aldoxime;
(1R,2R,3S)-3-(3,4-Dichlorophenyl)tropane-2-O-(1,1-dimethylethyl)-aldoxime;
(1R,2R,3S)-3-(4-Chlorophenyl)tropane-2-O-aldoxime;
(1R,2R,3S)-3-(4-Chlorophenyl)tropane-2-O-methylaldoxime hydrochloride;
(1R,2R,3S)-3-(4-Chlorophenyl)tropane-2-O-methoxycarbonylmethyl-aldoxime;
(1R,2R,3S)-3-(3,4-Dichlorophenyl)tropane-2-O-(2-propynyl)-aldoxime;
(1R,2R,3S)-3-(3,4-Dichlorophenyl)tropane-2-O-(2-methylpropyl)-aldoxime;
(1R,2R,3S)-3-(3,4-Dichlorophenyl)tropane-2-O-cyclopropylmethyl-aldoxime;
(1R,2R,3S)-3-(3,4-Dichlorophenyl)tropane-2-O-ethyl-aldoxime;
(1R,2R,3S)-2-Methoxymethyl-3-(3,4-dichlorophenyl)-tropane;
(1R,2R,3S)-2-Isopropoxymethyl-3-(3,4-dichlorophenyl)-tropane;
(1R,2R,3S)-2-Ethoxymethyl-3-(3,4-dichlorophenyl)-tropane;
(1R,2R,3S)-2-Cyclopropylmethyloxymethyl-3-(3,4-dichlorophenyl)-tropane;
(1R,2R,3S)-2-Methoxymethyl-3-(4-chlorophenyl)-tropane;
(1R,2R,3S)-N-Normethyl-2-methoxymethyl-3-(4-chlorophenyl)-tropane;
(1R,2R,3S)-2-Ethoxymethyl-3-(4-chlorophenyl)-tropane;
(1R,2R,3S)-N-Normethyl-2-methoxymethyl-3-(3,4-dichlorophenyl)-tropane;
(1R,2R,3S)-N-Normethyl-2-ethoxymethyl-3-(3,4-dichlorophenyl)-tropane;
(1R,2R,3S)-N-Normethyl-2-ethoxymethyl-3-(4-chlorophenyl)-tropane;
(1R,2R,3S)-N-Normethyl-2-cyclopropylmethyloxymethyl-3-(4-chlorophenyl)-tropane;
(1R,2R,3S)-2-Cyclopropylmethyloxymethyl-3-(4-chlorophenyl)-tropane;
(1R,2R,3S)-2-Ethylthiomethyl-3-(3,4-dichlorophenyl)-tropane;
(1R,2R,3S)-2-Hydroxymethyl-3-(4-fluorophenyl)tropane;
(1R,2R,3S)-2-Hydroxymethyl-3-(3,4-dichlorophenyl)tropane;
(1R,2R,3S)-N-Normethyl-N-(tert-butoxycarbonyl)-2-hydroxymethyl-3-(3,4-dichlorophenyl)tropane;
(1R,2R,3S)-2-Hydroxymethyl-3-(4-chlorophenyl)tropane;
(1R,2R,3S)-2-(3-(2-Furanyl)-1,2,4-oxadiazol-5-yl)-3-(3,4-dichlorophenyl)-tropane;
(1R,2R,3S)-2-(3-(3-Pyridyl)-1,2,4-oxadiazol-5-yl)-3-(3,4-dichlorophenyl)-tropane;
(1R,2R,3S)-N-Normethyl-N-allyl-2-(3-(4-pyridyl)-1,2,4-oxadiazol-5-yl)-3-(3,4-dichlorophenyl)-tropane;
(1R,2R,3S)-N-Normethyl-N-ethyl-2-(3-(4-pyridyl)-1,2,4-oxadiazol-5-yl)-3-(3,4-dichlorophenyl)-tropane;
(1R,2R,3S)-N-Normethyl-N-(2-hydroxyethyl)-2-(3-(4-pyridyl)-1,2,4-oxadiazol-5-yl)-3-(3,4-dichlorophenyl)-tropane;
(1R,2R,3S)-N-Normethyl-2-(3-(4-pyridyl)-1,2,4-oxadiazol-5-yl)-3-(3,4-dichlorophenyl)-tropane;
(1R,2R,3S)-N-Normethyl-N-allyl-2-(3-(3-pyridyl)-1,2,4-oxadiazol-5-yl)-3-(3,4-dichlorophenyl)-tropane;
(1R,2R,3S)-N-Normethyl-N-allyl-2-(3-(2-pyridyl)-1,2,4-oxadiazol-5-yl)-3-(3,4-dichlorophenyl)-tropane;
(1R,2R,3S)-2-(3-(2-Thienyl)-1,2,4-oxadiazol-5-yl)-3-(4-chlorophenyl)-tropane;
(1R,2R,3S)-2-(3-(2-Thienyl)-1,2,4-oxadiazol-5-yl)-3-(3,4-dichlorophenyl)-tropane;
(1R,2R,3S)-2-(3-(4-Pyridyl)-1,2,4-oxadiazol-5-yl)-3-(3,4-dichlorophenyl)-tropane;
(1R,2R,3S)-2-(3-(2-Pyridyl)-1,2,4-oxadiazol-5-yl)-3-(3,4-dichlorophenyl)-tropane;
(1R,2R,3S)-2-(3-(4-Pyridyl)-1,2,4-oxadiazol-5-yl)-3-(4-chlorophenyl)-tropane;
(1R,2R,3S)-2-(3-(3-Pyridyl)-1,2,4-oxadiazol-5-yl)-3-(4-chlorophenyl)-tropane;
(1R,2R,3S)-2-(3-(2-Pyridyl)-1,2,4-oxadiazol-5-yl)-3-(4-chlorophenyl)-tropane;
(1R,2R,3S)-2-(3-Phenyl-1,2,4-oxadiazol-5-yl)-3-(4-fluorophenyl)-tropane;
(1R,2R,3S)-2-(3-Phenyl-1,2,4-oxadiazol-5-yl)-3-(4-methylphenyl)-tropane;
(1R,2R,3S)-2-(3-Benzyl-1,2,4-oxadiazol-5-yl)-3-(4-fluorophenyl)-tropane;
(1R,2R,3S)-2-(3-(4-Phenylphenyl)-1,2,4-oxadiazol-5-yl)-3-(4-fluorophenyl)-tropane;
(1R,2R,3S)-2-(3-Phenyl-1,2,4-oxadiazol-5-yl)-3-(2-naphthyl)-tropane;
(1R,2R,3S)-2-(4-Chlorophenoxy-methyl)-3-(4-fluorophenyl)-tropane;
(1R,2R,3S)-2-(4-Chlorophenoxy-methyl)-3-(4-fluorophenyl)-tropane;
(1R,2R,3S)-2-(4-Chlorophenoxy-methyl)-3-(3,4-dichlorophenyl)-tropane;
(1R,2R,3S)-2-(4-Chlorophenoxy-methyl)-3-(4-methylphenyl)-tropane;
(1R,2R,3S)-2-(4-Benzoyloxy-methyl)-3-(4-fluorophenyl)-tropane;
(1R,2R,3S)-2-Carbomethoxy-3-(2-naphthyl)-tropane;
(1R,2R,3S)-2-Carbomethoxy-3-(3,4-dichlorophenyl)-tropane;
(1R,2R,3S)-2-Carbomethoxy-3-benzyl-tropane;
(1R,2R,3S)-2-Carbomethoxy-3-(4-chlorophenyl)-tropane;
(1R,2R,3S)-2-Carbomethoxy-3-(4-methylphenyl)-tropane;
(1R,2R,3S)-2-Carbomethoxy-3-(1-naphthyl)-tropane;
(1R,2R,3S)-2-Carbomethoxy-3-(4-phenylphenyl)-tropane;
(1R,2R,3S)-2-Carbomethoxy-3-(4-t-butyl-phenyl)-tropane;
(1R,2R,3S)-2-(4-Fluoro-benzoyl)-3-(4-fluorophenyl)-tropane;

or a pharmaceutically acceptable addition salt thereof.

In one embodiment, the tropane derivative having dopamine reuptake inhibitor activity is a compound of the general formula (II)

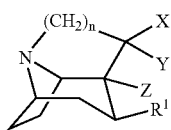

(II)

or any of its enantiomers or any mixture thereof, a pharmaceutically acceptable addition salt thereof or the N-oxide thereof wherein X and Y together forms =O, =S, =NOR², =CR³R⁴, =N—CN, =N—NR⁷R⁸, —(CH₂)$_m$—, or —W'—(CH₂)$_p$—W"—, or one of X and Y is hydrogen and the other is —OR⁵, —SR⁵, or —NR⁵R⁶ Z is hydrogen, —COOR⁹;

R³ and R⁴ are independently hydrogen, halogen, alkyl, cycloalkyl, cycloalkylalkyl, alkenyl, alkynyl, alkoxy, aryl, arylalkyl, or —(CH₂)$_q$—COOR²;

R², R⁵ and R⁶ are independently hydrogen, alkyl, cycloalkyl, cycloalkylalkyl, alkenyl, alkynyl, aryl, or arylalkyl, —CO-alkyl, or —SO₂-alkyl;

R⁷ and R⁸ are independently hydrogen, alkyl, cycloalkyl, cycloalkylalkyl, alkenyl, alkynyl, aryl, or arylalkyl;

R⁹ is alkyl, alkenyl or alkynyl;

R¹ is alkyl, alkenyl, alkynyl, aryl, or arylalkyl;

where said aryl groups may be substituted one or more times with substituents selected from the group consisting of halogen, CF₃, CN, alkoxy, cycloalkoxy, alkyl, cycloalkyl, alkenyl, alkynyl, amino, alkylamino, dialkylamino and nitro;

W' and W" are each independently O or S;

n is 1, 2, 3, or 4;

m is 2, 3, 4, or 5;

p is 1, 2, 3, 4, or 5; and q is 0, 1, 2, 3, or 4.

In a special embodiment, the tropane derivative having dopamine reuptake inhibitor activity is a compound of the general formula (II) selected from:

(1S,2S,4S,7R)-2-(3,4-Dichlorophenyl)-8-azatricyclo[5.4.0.0⁴,⁸]undecan-11-one;

(1S,2S,4S,7R)-2-(3,4-Dichlorophenyl)-8-azatricyclo[5.4.0.0⁴,⁸]undecan-11-ol;

(1S,3S,4S,8R)-3-(3,4-Dichlorophenyl)-7-azatricyclo[5.3.0.0⁴,⁸]decan-5-one;

(1S,3S,4S,8R)-3-(3,4-Dichlorophenyl)-7-azatricyclo[5.3.0.0⁴,⁸]decan-5-one O-methyl-oxime;

(1S,2S,4S,7R)-2-(4-Chlorophenyl)-8-azatricyclo[5.4.0.0⁴,⁸]undecan-11-one;

(1S,3S,4S,8R)-3-(3,4-Dichlorophenyl)-7-aza-tricyclo[5.3.0.0⁴,⁸]decan-5-ol;

(1S,3S,4S,8R)-3-(3,4-Dichlorophenyl)-7-azatricyclo[5.3.0.0⁴,⁸]dec-5-yl acetate;

(1S,3S,4S,8R)-3-(3,4-Dichlorophenyl)-7-azatricyclo[5.3.0.0⁴,⁸]dec-5-yl methane sulphate;

(1S,3S,4S,8R)-3-(3,4-Dichlorophenyl)-5-methoxy-7-azatricyclo[5.3.0.0⁴,⁸]decane;

(1S,3S,4S,8R)-3-(3,4-Dichlorophenyl)-5-ethoxy-7-azatricyclo[5.3.0.0⁴,⁸]decane;

(1S,3S,4S,8R)-3-(4-Chlorophenyl)-7-azatricyclo[5.3.0.0⁴,⁸]decan-5-one;

(1S,3S,4S,8R)-3-(4-Chlorophenyl)-7-azatricyclo[5.3.0.0⁴,⁸]decan-5-ol;

(1S,3S,4S,8R)-3-(4-Chlorophenyl)-5-ethoxy-7-azatricyclo[5.3.0.0⁴,⁸]decane;

(1S,3S,4S,8R)-3-(3,4-Dichlorophenyl)-7-azatricyclo[5.3.0.0⁴,⁸]decan-5-one O-benzyl-oxime;

(1S,3S,4S,8R)-3-(3,4-Dichlorophenyl)-7-azatricyclo[5.3.0.0⁴,⁸]decan-5-one O-allyl-oxime;

(1S,3S,4S,8R)-3-(3,4-Dichlorophenyl)-7-azatricyclo[5.3.0.0⁴,⁸]decan-5-one oxime;

(1S,3S,4S,8R)-3-(3,4-Dichlorophenyl)-7-azatricyclo[5.3.0.0⁴,⁸]decan-5-one O-tert.-butyl-oxime;

(1S,3S,4S,8R)-3-(3,4-Dichlorophenyl)-7-azatricyclo[5.3.0.0⁴,⁸]decan-5-one O-ethyl-oxime;

(1S,3S,4S,8R)-5-Allyloxy-3-(3,4-dichlorophenyl)-7-azatricyclo[5.3.0.0⁴,⁸]decane;

Ethyl (1S,3S,4S,8R)-2-[3-(3,4-dichlorophenyl)-7-azatricyclo[5.3.0.0⁴,⁸]dec-5-yliden]acetate;

(1S,3S,4S,8R)-3-(4-Chlorophenyl)-7-azatricyclo[5.3.0.0⁴,⁸]decan-5-one oxime;

N1-[1S,3S,4S,8R)-3-(4-Chlorophenyl)-7-azatricyclo[5.3.0.0⁴,⁸]dec-5-yl]acetamide;

(1S,3S,4S,8R)-3-(3,4-Dichlorophenyl)-7-azatricyclo[5.3.0.0⁴,⁸]dec-5-yl amine;

or a pharmaceutically acceptable addition salt thereof.

In one further embodiment, the disease to be treated, prevented or alleviated is selected from ischemic diseases, anoxic episodes, and injury to the brain and other parts of the CNS caused by trauma or other injury, for example a blow to the head. In such reduced blood flow episodes, or episodes where there is a temporary break in blood supply, oxygen supply to the brain is reduced or interrupted.

In a further embodiment, the disease to be treated, prevented or alleviated is selected from cerebrovascular disorders such as cerebral ischemia or cerebral infarction resulting from a range of conditions, such as tromboembolic or haemorrhagic stroke, cerebral vasospasm, hypoglycaemia, cardiac arrest, perinatal asphyxia, anoxia such as from near-drowning, pulmonary surgery and cerebral trauma.

The method can be used in the treatment or prevention of traumatic brain injury, in particular ischemic, hypoxic or anoxic brain damage, spinal cord injury, tissue ischemia and reperfusion injury in a mammal at risk for such damage.

The brain damage may follow or be caused by: cerebral ischemia, cardiac arrest, high-risk surgery such as cardiac surgery, stroke, neonatal hypoxia, hypoxia caused by compromised lung function, neonatal anoxia, anoxia caused by compromised lung function, cerebral trauma, secondary regional ischemia induced by brain oedema, increased intercranial pressure, open brain surgery, endarterectomy, surgical interventions involving temporary, artificially sustained arrest of cardiopulmonary functions resulting in impairment of cerebral blood flow, and emergency treatment involving cardiopulmonary resuscitation (CPR).

In a special embodiment, the disease to be treated, prevented or alleviated is acute treatment of ischemic stroke, treatment of brain damage following global cerebral ischemia, or prevention of brain damage following high risk surgery.

In many instances of brain ischemia, treatment is not available to the patient for several, e.g. up to 6 hours, in stroke patients typically 3 to 6 hours, after the ischemic injury. Such a delay places great demands on any therapeutic regime designed to mitigate ischemic brain injury. It has been found, however, that the tropane derivative having dopamine reuptake inhibitor activity for use according to the invention is surprisingly effective whether administered pre-ischemically or post-ischemically.

When administered post-ischemically it is advisable that the tropane derivative having dopamine reuptake inhibitor activity be administered within one day of the ischemic insult. Although the tropane derivative having dopamine reuptake inhibitor activity used in the invention may be administered as late as 14 hours after brain reperfusion, the treatment should preferably be carried out within 12 hours of ischemic alleviation or reperfusion. Preferably, the treatment should occur within 6 hours of alleviation of ischemia. Yet more preferred is the administration of the tropane derivative having dopamine reuptake inhibitor activity used in the invention within 3 hours of alleviation of ischemia As used herein, CNS includes the brain and spinal cord and combating includes both therapy and diagnosis.

Tropane Derivatives having Dopamine Reuptake Inhibitor Activity

The potential of a given substance to act as a dopamine reuptake inhibitors activity may be determined using standard in vitro binding assays and/or standard in vivo functionality tests, such as those described in "Test methods".

The tropane derivative having dopamine reuptake inhibitor activity for use according to the invention may in particular be tropane derivatives such as those disclosed the NeuroSearch patent applications EP 604355, EP 604352, U.S. Pat. No. 5,444,070, EP 604354, WO 95/28401, and WO 97/30997, and fused tropane derivatives such as those disclosed NeuroSearch application WO 97/16451.

In one embodiment, the tropane derivative having dopamine reuptake inhibitor activity shows an $IC_{50}$ value of less than 1 µM, preferably less than 100 nM, more preferably less than 50 nM, and even more preferably less than 10 nM when tested for in vitro inhibition of $^3$H-DA uptake (test method 1).

In a second embodiment, the tropane derivative having dopamine reuptake inhibitor activity shows an $ED_{50}$ value of less than 500 mg/kg, preferably less than 100 mg/kg, more preferably less than 50 mg/kg, more preferably less than 20 mg/kg, and even more preferably less than 10 mg/kg when tested for in vivo inhibition of $^3$H-WIN 35428 binding p.o., s.c. or i.p. (test method 5).

In a further embodiment, the tropane derivative having dopamine reuptake inhibitor activity shows a protection against MPTP of more than 60%, preferably more than 70%, and even more preferably more than 80% at 20 mg/kg of the test substance when tested for effect on striatal dopamine in mice treated with MPTP (test method 8). In a still further embodiment, the tropane derivative having dopamine reuptake inhibitor activity shows a protection against MPTP of more than 60%, preferably more than 70%, and even more preferably more than 80% at 10 mg/kg of the test substance when tested for effect on striatal dopamine in mice treated with MPTP.

The above examples of tropane derivative having dopamine reuptake inhibitor activity are not intended to be in any way limiting to the scope of the invention as claimed.

Definition of Substituents

In the context of this invention alkyl designates a straight chain or a branched chain containing of from one to six carbon atoms ($C_1$-$C_6$ alkyl), including but not limited to methyl, ethyl, propyl, isopropyl, butyl, isobutyl, t-butyl, pentyl and hexyl. In a preferred embodiment of this invention alkyl represents a $C_1$-$C_4$ alkyl, preferably a $C_1$-$C_3$ alkyl, most preferred methyl, ethyl, propyl or isopropyl.

In the context of this invention cycloalkyl designates a cyclic alkyl containing of from three to seven carbon atoms ($C_3$-$C_7$ cycloalkyl), including but not limited to cyclopropyl, cyclobutyl, cyclopentyl, and cyclohexyl.

In the context of this invention alkenyl designates a group containing of from two to six carbon atoms ($C_2$-$C_6$ alkenyl), including at least one double bond, for example, but not limited to ethenyl, 1,2- or 2,3-propenyl, 1,2-, 2,3-, or 3,4-butenyl.

In the context of this invention alkynyl designates a group containing of from two to six carbon atoms ($C_2$-$C_6$ alkynyl), including at least one triple bond, for example, but not limited to ethynyl, 1,2- or 2,3-propynyl, 1,2-, 2,3- or 3,4-butynyl.

In the context of this invention cycloalkyl-alkyl designates a cycloalkyl as defined above which is attached to an alkyl as also defined above, e.g. cyclopropylmethyl.

In the context of this invention aryl designates an aromatic hydrocarbon, such as phenyl or naphthyl.

In the context of this invention alkoxy designates an alkyl-O—, where alkyl is as defined above.

In the context of this invention acyl designates an alkyl-CO—, where alkyl is as defined above.

In the context of this invention halogen designates a fluorine, a chlorine, a bromine or an iodine atom.

In the context of this invention amino represents $NH_2$, NH-alkyl, or N-(alkyl)$_2$, wherein alkyl is as defined above.

In the context of this invention heteroaryl designates a 5- or 6-membered heterocyclic monocyclic group, for example, but not limited to, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1,2,5-thiadiazol4-yl, 2-imidazolyl, 4-imidazolyl, 5-imidazolyl, 2-pyrrolyl, 3-pyrrolyl, 2-furanyl, 3-furanyl, 2-thienyl, 3-thienyl, 2-pyridyl, 3-pyridyl, 4-pyridyl.

Steric Isomers

The chemical compounds for use in the invention may exist in (+) and (−) forms as well as in racemic forms. The use of racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l-(tartrates, mandelates, or camphor-sulphonate) salts for example.

The chemical compounds for use in the invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Moreover, some of the chemical compounds for use in the invention may thus exist in two forms, syn- and anti-form (Z- and E-form), depending on the arrangement of the substituents around a —C=C— or —C=N— double bond. A chemical compound for use according to the present invention may thus be the syn- or the anti-form (Z- and E-form), or it may be a mixture hereof.

Pharmaceutically Acceptable Salts

The tropane derivative having dopamine reuptake inhibitor activity for use according to the invention may be provided in any form suitable for the intended administration. Suitable forms include pharmaceutically (i.e. physiologically) acceptable salts, and pre- or prodrug forms of the chemical compound for use according to the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Metal salts of a chemical compound for use according to the invention include alkali metal salts such as the sodium salt of the chemical compound containing a carboxy group.

The term "prodrug" denotes a compound, which is a drug precursor and which, following administration and absorption, release the drug in vivo via some metabolic process.

Particularly favoured prodrugs are those that increase the bioavailability of the compounds for use according to the invention (e.g. by allowing an orally administrered compound to be more readily absorbed into the blood) or which enhance delivery of the parent compound to a specific biological compartment (e.g. the brain or lymphatic system).

Thus examples of suitable prodrugs of the substances according to the invention include compounds modified at one or more reactive or derivatizable groups of the parent compound. Of particular interest are compounds modified at a carboxyl group, a hydroxyl group, or an amino group. Examples of suitable derivatives are esters or amides.

Pharmaceutical Compositions

The invention provides the use of pharmaceutical compositions comprising a therapeutically effective amount of the dopamine reuptake inhibitor. While a tropane derivative having dopamine reuptake inhibitor activity for use in therapy according to the invention may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the tropane derivative having dopamine reuptake inhibitor activity, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition can be manufactured by any skilled person by use of standard methods and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Combined Treatment

The pharmaceutical composition for use according to the invention may include or may be used or administered in combination with one or more additional drugs useful for the treatment, prevention or alleviation of a disease associated with reduced blood flow to the brain or with an instance of a temporary break in blood supply to the brain. Such additional drugs include compounds capable of blocking excitatory amino acid receptors (glutamate and aspartate) and neurotrophic compounds Examples of compounds capable of blocking excitatory amino acid receptors include those substances described in the patent applications WO 94/26747, WO 96/08494, WO 96/08495, WO 98/14447 and WO 99/49864 (all NeuroSearch).

In the context of this invention, compounds with neurotrophic activity are compounds that mimic or enhance the function of one or more endogenous neurotrophic factors. In one embodiment, a compound with neurotrophic activity is a compound that mimics or enhances the function of NGF, BDNF, and/or GDNF. In a further embodiment, a compound with neurotrophic activity is a compound that mimics or enhances the function of bFGF and/or EGF. In a special embodiment, a compound with neurotrophic activity is a compound that mimics or enhances the function of NGF. The neurotrophic activity has not been ascribed to a specific step in the interaction between the growth factor and its receptor or in the growth factor signal transduction pathway. The potential of a given substance to act as a compound with neurotrophic activity may be determined using standard in vitro binding assays and/or standard in vivo functional tests.

Compounds with neurotrophic activity include those substances described in the patent applications WO 98/07705

(Takeda Chem Ind Ltd), WO 00/34262 (Takeda Chem Ind Ltd), WO 00/32197 (Alcon Lab Inc), WO 97/40035 (NeuroSearch), WO 00/43397 (NeuroSearch), international application WO 01/55110 (NeuroSearch), JP 2000226388-A (Takeda Chem Ind Ltd), WO 00/32197 (Alcon Lab), and WO 00/46222 (Schering AG).

Further examples of compounds with neurotrophic activity according to the invention include 1-(1,3-benzodioxol-5-yl)-7,8,9,10-tetrahydro-1,3-benzodioxol[4,5-g]isoquinolin-7-one (Takeda), 2-(2,2,4,6,7-Pentamethyl-3-phenyl-2,3-dihydro-1-benzo-furan-5-yl)-isoindoline (Takeda), 4-Aryl-1-phenylalkyl-1,2,3,6-tetrahydropyridine (Sanofi-Synthelabo), SR-57746A or 1-(2-napht-2-yl)ethyl-4-(3-trifluoromethylphenyl)-1,2,5,6-tetrahydropyridine (Sanofi-Synthelabo), AIT-082 (NeoTherapeutics), NIL-A (Amgen Inc), K-252a (Cephalon), CEP-1347, GPI-1046 (Guilford), CTQ3, CTQ5 and CTQ8 (Centre de Neurochimie du CNRS), V-10,367 and V-13,661 (Vertex Pharmaceuticals Inc), ABS-205 (American Biogenic Sciences), Dexanabinol or HU-211 (Pharmos), or salts, free bases, racemates or enantiomers thereof.

The above examples of compounds capable of blocking excitatory amino acid receptors and compounds with neurotrophic activity are not intended to be in any way limiting to the scope of the invention.

Methods of Preparation

The compounds of general formula (I) and (II) for use in the invention may be prepared by conventional methods of chemical synthesis, e.g. those described in the NeuroSearch patent publications EP 604355, EP 604352, U.S. Pat. No. 5,444,070, EP 604354, WO 97/30997, WO 95/28401, and WO 97/16451.

The starting materials for the processes described in the present application are known or may readily be prepared by conventional methods from commercially available chemicals.

The end products of the reactions described herein may be isolated by conventional techniques, e.g. by extraction, crystallisation, distillation, chromatography, etc.

Any possible combination of two or more of the embodiments described in this patent application is comprised within the scope of the present invention.

The invention is further illustrated with reference to the following test methods and examples which are not intended to be in any way limiting to the scope of the invention as claimed.

Test Methods

Method 1

In Vitro Inhibition of $^3$H-dopamine ($^3$H-DA) Uptake in Striatal Synaptosomes In this test, the ability of dopamine reuptake inhibitor (below: the test compound) to inhibit the uptake of $^3$H-dopamine in striatal synaptosomes is assessed.

Tissue preparations: Preparations are performed at 0-4° C. unless otherwise indicated. Corpi striati from male Wistar rats (150-200 g) are homogenised for 5-10 sec in 100 volumes of ice-cold 0.32M sucrose containing 1 mM pargyline using an Ultra-Turrax homogenizer. Monoamine oxidase activity will be inhibited in the presence of pargyline. The homogenate is centrifuged at 1000×g for 10 min. The resulting supernatant is then centrifuged at 27,000×g for 50 min and the supernatant is discarded. The pellet ($P_2$) is resuspended in oxygenated (equilibrated with an atmosphere of 96% $O_2$:4% $CO_2$ for at least 30 min) Krebs-Ringer incubation buffer (8000 ml per g of original tissue) at pH 7.2 containing 122 mM NaCl, 0.16 mM EDTA, 4.8 mM KCl, 12.7 mM $Na_2HPO_4$, 3.0 mM $NaH_2PO_4$, 1.2 mM $MgSO_4$, 1 mM $CaCl_2$, 10 mM glucose and 1 mM ascorbic acid.

Assay: Aliquots of 4.0 ml tissue suspension are added to 100 μl of test solution and 100 μl of $^3$H-DA (1 nM, final concentration), mixed and incubated for 25 min at 37° C. Non-specific uptake is determined using benztropine (10 μM, final concentration). After incubation the samples are poured directly onto Whatman GF/C glass fibre filters under suction. The filters are then washed three times with 5 ml of ice-cold 0.9% (w/v) NaCl solution. The amount of radioactivity on the filters is determined by conventional liquid scintillation counting. Specific uptake is calculated as the difference between total uptake and non-specific uptake.

25-75% inhibition of specific binding must be obtained, before calculation of an $IC_{50}$. The test value is given as $IC_{50}$ (the concentration (μM) of the test compound which inhibits the specific binding of $^3$H-DA by 50%).

Method 2

Inhibition of DA Uptake in Rat Brain Synaptosomes

In this method the ability of test compounds to inhibit the activity of dopamine transporter proteins is measured in vitro by analyzing the synaptosomal uptake of [$^3$H]dopamine ([$^3$H]DA).

Tissue Preparation: Preparations are performed at 0-4° C. unless otherwise indicated. The striata from male Wistar rats (150-200 g) are homogenized for 5-10 sec in 100 volumes of ice-cold 0.32 M sucrose containing 1 mM pargyline using a motor driven teflon pestle in a glass homogenizing vessel. Monoamine oxidase activity is inhibited in the presence of pargyline. The homogenates are centrifuged at 1000×g for 10 min. The resulting supernatants are then centrifuged at 27,000×g for 50 min. The supernatants are discarded and the pellets ($P_2$) are resuspended in oxygenated (equilibrated with an atmosphere of 96% $O_2$:4% $CO_2$ for at least 30 min) Krebs-Ringer incubation buffer (pH 7.2) (8000 ml per g of original tissue for the [$^3$H]DA assay) containing 122 mM NaCl, 0.16 mM EDTA, 4.8 mM KCl, 12.7 mM $Na_2HPO_4$, 3.0 mM $NaH_2PO_4$, 1.2 mM $MgSO_4$, 0.97 mM $CaCl_2$, 10 mM glucose and 1 mM ascorbic acid.

Uptake assays: Aliquots of 4.0 ml tissue suspension are added to 0.1 ml of test solution and 0.1 ml of [$^3$H]DA (1 nM, final concentration), mixed and incubated for 25 min at 37° C. Non-specific uptake is determined in the presence of benztropine (1 μM, final concentration). After incubation the samples are poured directly onto Whatman GF/C glass fibre filters under suction. The filters are then washed three times with 5 ml of ice-cold 0.9% (w/v) NaCl solution. The amount of radioactivity on the filters is determined by conventional liquid scintillation counting using a Tri-carb™ liquid scintillation analyzer (model 1600CA; Packard, USA) Specific uptake is calculated as the difference between total uptake and non-specific uptake.

Data analysis: The test value is given as an $IC_{50}$ (the concentration (μM) of the test substance which inhibits the specific uptake of [$^3$H]ligand by 50%). Three concentrations are been used to determine the inhibition curves from which the $IC_{50}$ values are determined. If a full curve is not available a 25-75% inhibition of specific binding must be obtained, before calculation of an $IC_{50}$.

$$IC_{50} = \text{(applied test substance concentration, } \mu M) \times \frac{1}{\left(\frac{C_o}{C_x} - 1\right)}$$

where $C_o$ is specific uptake in control assays and $C_x$ is the specific uptake in the test assay. (The calculations assume normal mass-action kinetics).

Method 3

Inhibition of In Vitro [$^3$H]GBR 12935 Binding to the Dopamine Transporter in Rat Striatal Synaptosomes In this method the ability of test compounds to inhibit the binding of GBR 12935 to the dopamine transporter in vitro is assessed.

Tissue preparation: Preparations are performed at 0-4° C. unless otherwise indicated. Striata from male Wistar rats (150-200 g) are homogenized for 5-10 sec in 10 ml Tris-citrate buffer (50 mM, pH 7.1) using an Ultra-Turrax homogenizer. The suspension is centrifuged at 27,000×g for 15 min. The supernatant is discarded and the pellet is resuspended in Tris-citrate buffer containing 120 mM NaCl and 4 mM MgCl$_2$ (7000 ml per g of original tissue) and used for binding assays.

Binding assays: Aliquots of 1.0 ml tissue suspension are added to 0.050 ml of test solution and 0.050 ml of [$^3$H]GBR 12935 (0.5 nM, final concentration), mixed and incubated for 60 min at 2° C. Non-specific binding is determined using GBR 12909 (1 µM, final concentration).

After incubation 5 ml of ice-cold buffer is added to the samples and poured directly onto Whatman GF/C glass fiber filters (for the [$^3$H]GBR 12935 assay the filters are pre-soaked in 0.1% PEI for at least 20 min) under suction and immediately washed with 5 ml ice-cold buffer. The amount of radioactivity on the filters is determined by conventional liquid scintillation counting using a Tri-carb liquid scintillation analyzer (model 1600CA; Packard, USA). Specific binding is calculated as the difference between total binding and non-specific binding.

Data analysis: The test value is given as an IC$_{50}$ (the concentration (µM) of the test substance which inhibits the specific binding of [$^3$H]ligand by 50%). Five to nine concentrations are been used to determine the inhibition curves from which the IC$_{50}$ values are determined. If a full curve is not available a 25-75% inhibition of specific binding must be obtained, before calculation of an IC$_{50}$.

$$IC_{50} = \text{(applied test substance concentration, } \mu M) \times \frac{1}{\left(\frac{C_o}{C_x} - 1\right)}$$

where $C_o$ is specific binding in control assays and $C_x$ is the specific binding in the test assay. (The calculations assume normal mass-action kinetics).

Method 4

Inhibition of In Vitro [$^3$H]WIN 35428 Binding to the Dopamine Transporter in Rat Striatal Synaptosomes In this method the ability of test compounds to inhibit the binding of WIN 35428 to the dopamine transporter in vitro is assessed.

Tissue preparation: Striata from male Wistar rats (150-200 g) are homogenized for 5-10 sec in 10 ml NaH$_2$PO$_4$ (50 mM, pH 7.4) using an Ultra-Turrax homogenizer. The suspension is centrifuged at 27,000×g for 15 min. The supernatant is discarded and the pellet is resuspended in phosphate buffer (1000 ml per g of original tissue) and used for binding assays.

Binding assays: Aliquots of 0.5 ml tissue suspension are added to 0.025 ml of test solution and 0.025 ml of [$^3$H]WIN 35428 (1 nM, final concentration), mixed and incubated for 60 min at 2° C. Non-specific binding is determined using cocaine (30 µM, final concentration).

After incubation 5 ml of ice-cold buffer is added to the samples and poured directly onto Whatman GF/C glass fiber filters (for the [$^3$H]GBR 12935 assay the filters are pre-soaked in 0.1% PEI for at least 20 min) under suction and immediately washed with 5 ml ice-cold buffer. The amount of radioactivity on the filters is determined by conventional liquid scintillation counting using a Tri-carb liquid scintillation analyzer (model 1600CA; Packard, USA). Specific binding is calculated as the difference between total binding arid non-specific binding.

Data analysis: The test value is given as an IC$_{50}$ (the concentration (µM) of the test substance which inhibits the specific binding of [$^3$H]ligand by 50%). Five to nine concentrations are been used to determine the inhibition curves from which the IC$_{50}$ values are determined. If a full curve is not available a 25-75% inhibition of specific binding must be obtained, before calculation of an IC$_{50}$.

$$IC_{50} = \text{(applied test substance concentration, } \mu M) \times \frac{1}{\left(\frac{C_o}{C_x} - 1\right)}$$

where $C_o$ is specific binding in control assays and $C_x$ is the specific binding in the test assay. (The calculations assume normal mass-action kinetics).

Method 5

Inhibition of In Vivo [$^3$H]WIN 35428 Binding

The test substance is administered to groups of three female NMRI mice (25 g) at specified time points, either i.v., i.p., s.c. or p.o. Forty-five min before decapitation the mice are injected i.v. via the tail vein with 2.0 µCi of [$^3$H]WIN 35428 in 0.25 ml saline. At the time of decapitation the striata are rapidly dissected on ice. Each striatum is weighed and dissolved for 36 h with 1 ml of 2% sodium-laurylsulfate. Two ml of scintillation cocktail is added to the solubilized tissue, and the amount of radioactivity per mg of tissue is determined by conventional liquid scintillation counting using a Tri-carb™ liquid scintillation analyzer (model 1600CA; Packard, USA). Groups of vehicle treated mice serves as controls. To determine non-specific binding, groups of mice are injected with WIN 35428 (2.5 mg/kg i.p.; 0.75 ml) at the time of [$^3$H]WIN 35428 injection. Specific binding is calculated as the difference between binding in vehicle and WIN 35428 treated mice.

Data analysis: The test value is given as an ED$_{50}$ (the dose (mg/kg) of the test substance which inhibits the specific binding of [$^3$H]WIN 35428 by 50%). Three doses of test substance are used to determine the dose response curve from which the ED$_{50}$ value is determined. If a full curve is not available a 25-75% inhibition of specific binding must be obtained before calculation of an ED$_{50}$ value.

$$ED_{50} = (\text{administered test substance dose, mg/kg}) \times \frac{1}{\left(\frac{C_o}{C_x} - 1\right)}$$

where $C_o$ is specific binding in controls and $C_x$ is the specific binding in mice treated with test substance.

Method 6

Protection of the Hippocampus after Transient Global Ischaemia in Gerbils

In this experiment, the neuroprotective effect of a test compound is assessed in an animal model of transient global ischaemia.

Method: In halothane anaesthetised gerbils, right and left carotid arteries are located and occluded for 4 minutes. Animals are kept at normal body temperature before and after the operation using heating lamps. During surgery, the gerbils are placed on heating pads, the body temperature is controlled and maintained at 37±0.5° C. The test compound is dosed at specified time points after the ischaemic insult, either i.v., i.p., s.c. or p.o.

Four days later, the animals are sacrificed, brains removed and cooled to −70° C. Thereafter, the brains are sectioned in 20 μm thick sections of which 5-7 with hippocampal tissue are selected and stained with hematoxylin-eosin.

The degree of hippocampal damage is categorised into one of four groups:

Group 1: no damage in the $CA_1$-layer;
Group 2: the $CA_1$-layer partly damaged;
Group 3: the $CA_1$-layer completely damaged; and
Group 4: damage in more than just the $CA_1$-layer.

The total ischaemia score is obtained as the sum of scores in the right- and left hemisphere. Kendall's tau test was used for statistic evaluation.

Method 7

Protection of the Substantia Nigra after Transient Global Ischaemia in Gerbils

In this experiment, the neuroprotective effect of a test compound is assessed in an animal model of transient global ischaemia.

Method: In halothane anaesthetised gerbils, right and left carotid arteries are located and occluded for 10 minutes. Animals are kept at normal body temperature before and after the operation using heating lamps. During surgery, the gerbils are placed on heating pads, the body temperature is controlled and maintained at 37±0.5° C. The test compound is dosed at specified time points after the ischaemic insult, either i.v., i.p., s.c. or p.o.

Fourteen days later, the animals are sacrificed, brains removed and cooled to −70° C. Thereafter, the brains are sectioned in 20 μm thick sections through the substantia nigra region. Sections are stained for tyroxine hydroxylase (TH+) expression using immunohistochemistry. The number of TH+ cells in the sections is counted and the total number of TH+ cells in the substantia nigra is calculated by means of stereology.

Method 8

Transient Global Ischaemia in Gerbils

In this experiment, the neuroprotective effect of a test compound is assessed in an animal model of transient global ischaemia.

Method: In halothane anaesthetised gerbils, right and left carotid arteries are located and occluded for 4 minutes. Animals are kept at normal body temperature before and after the operation using heating lamps. During surgery, the gerbils are placed on heating pads, the body temperature is controlled and maintained at 37±0.5° C. The test compound is dosed at specified time points after the ischaemic insult, either i.v., i.p., s.c. or p.o.

Four days later, the animals are sacrificed, brains removed and cooled to −70° C. Thereafter, the brains are sectioned in 20 μm thick sections of which 5-7 with hippocampal tissue are selected and stained with hematoxylin-eosin.

The degree of hippocampal damage is categorised into one of four groups:

Group 1: no damage in the $CA_1$-layer;
Group 2: the $CA_1$-layer partly damaged;
Group 3: the $CA_1$-layer completely damaged; and
Group 4: damage in more than just the $CA_1$-layer.

The total ischaemia score is obtained as the sum of scores in the right- and left hemisphere. Kendall's tau test was used for statistic evaluation.

Method 9

Mouse Middle Cerebral Artery Occlusion (MCAO)

In this experiment, the neuroprotective effect of a compound is assessed in an animal model of focal ischaemia.

Female NMRI-mice (27-38 g) are anaesthetized with halothane (2% halothane in 30% $O_2$-70% $NO_2$). During surgery the body temperature is maintained at 37±0.5° C. by placing the mice on heating pads connected to a CMA/150 temperature controller. MCAO is performed as earlier described (Møller et al., Neurol Res, 17, 353-360, 1995). After MCAO, the mice are placed under heating lamps. The test compound is administered at specified time points after the ischaemic insult, either i.v., i.p., s.c. or p.o. The control group is given vehicle. On the fourth day, the mice are sacrificed and the brains removed. The brains are frozen on dry ice and cut into 20 μm sections. Every $40^{th}$ sections are sampled and the total infarct volume is used as the endpoint for ischemic damage. The infarct volume is estimated using the Cavalieri's volume estimator (Gundersen et al., AMPIS, 96, 379-394, 1998).

Method 10

Effect of a Compound on Striatal Dopamine in Mice Treated with MPTP

In this test, the ability of compound to increase striatal dopamine in mice treated with MPTP is assessed.

Female C57BL/6J mice weighing 20-25 grams (Møllegaard Breeding and Research Centre) are adapted to the laboratory for 5-7 days before the experiments with food and water freely available, room temperature 22-24° C. Light is on/off at 7 am and 6 pm, respectively. At least 5-8 mice are used per group. MPTP, HCL (RBI) is dissolved in saline just before the experiments and is tested in various doses 12.5, 25, 3×12.5 and 3×25 mg/kg sc. The test compound is tested following a pretreatment time between 30 min and 3 hrs before the subcutaneous sc injection of MPTP 25 mg/kg. The mice are sacrificed 48 hrs after the last dose of MPTP for the biochemical analysis of dopamine and its metabolites HVA and DOPAC. For biochemical analysis, the striatum of the mice is rapidly dissected out, frozen and stored at −80° C. On the day of analysis, one striatum per mouse (weighing 5-7 mg) is homogenised in 1 ml of 0.1 N Perchloric acid containing 5% EDTA. After centrifugation 14,0000×G for 30 min. 200 μl of the supernatant is filtered through a glass 0.22 μm filter. 20 μl is then injected into our ESA Coulochem II HPLC equipment with a the following column (Caracholamine HR-80 4.6 mm×80 mm 3 um Nucleosil C 18). The eluent is 10.25 g $NaH_2PO_4$, 185 mg EDTA, 100 mg Octansulphonic acid. 9% methanol, pH 3.7, add 500 ml MiliQ water, filtered through 0.22 um. The Colochem ESA analytical cell is 5014A and the ESA detector has the following settings: $E_2$ −175 mV, run time 16 min. for the elution of dopamine, DOPAC and HVA (DOPAC=4.3 min; dopamine=6.4 min and HVA=12.7 min.). The autoinjector SHIMADZY sil-10A has the following settings; injection vol. 20 μl, 16 min analysis, temp 4° C. Flow rate from the pump is 0.80 ml/min. The analyses are calibrated with standards of 3 pM of dopamine, HVA and DOPAC for each 12 analysis run and are compared with our standard curves.

Method 11

Effect of a Compound on Extracellular Dopamine Measured by Microdialysis

In this test, the ability of a compound to increase dopamine in various brain regions is assessed.

Male SPF Mol Wistar rats weighing 300-350 g are obtained from Møllegaard Breeding and Research Centre and housed in standard Macrolon cages sized 24×36×18 cm for at least 5 days under standard conditions at a temperature of 23±2° C. and a humidity of 60%±10%, and a 12 h light and dark cycle. The rats are housed in groups of two with food and water freely available ad libitum. For microdialysis, the rat is placed in a stereotaxic instrument under halothane anesthesia using 1½% halothane, 20% oxygen and 80% nitrous oxide. The rectal temperature is monitored and maintained at 37.0±1° C. during the experimental period using a heating pad (CMA 150 Carnegie Medicin). A small hole is drilled to allow a vertical probe (CMA/123), to be stereotaxically implanted into the right striatum, using the following coordinates relative to bregma: AP +1 mm; L 3 mm; DV −6 mm. The probes for the nucleus accumbens (CMA 122) is implanted vertical at the following coordinates: AP +2.4, L1.4 and DV −8 mm. Similar experiments are performed with probes implanted into the nucleus accumbens in non anaesthetised freely moving animals. These experiments are performed 48 h after surgery during the daylight period in animals housed individually in plastic cages with food and water available ad libitum. In all cases, the injection sites are confirmed histologically according to the atlas of Paxinos and Watson.

After an initial 2 h period, samples of dialysate are collected from halothane anaesthetised rats. The dosing of a test compound to these rats are usually initiated after the collection of 3 base line analyses. Dopamine and its metabolites are rapidly frozen to −18° C. and then analyzed as soon as possible thereafter. The dialysis probe is perfused at a rate of 2 μl/min (by a CMA/100 microperfusion pump) with Ringer's solution (147 mM NaCl, 4 mM KCl, 2.3 mM CaCl) i.e. Ringer's solution (NaCl 4.3 g, KCl 150 mg, $CaCl_2$ 110.3 mg ad 500 ml) adjusted to pH 6.5 with 2 mM sodium phosphate buffer. The Ringer solution is filtered before use through Millipore glass filters (0.22 μm). The dialysate fractions (40 μl) are collected at 20 min intervals and then injected into the HPLC system. The concentration of dopamine (DA), dihydroxy phenyl acetic acid (DOPAC), homovanillic acid (HVA) and 5-hydroxy indolacetic acid (5-HIAA) are determined by high-performance liquid chromatography with electrochemical detection (HPLC-ED). The column is a reverse-phase liquid chromatography Catecholamine 3 μm ESA column at 23° C., the mobile phase consisting of 0.055 M sodium acetate with 0.1 nM octanesulfonic acid, 0.01 mM Na EDTA, and 10% methanol pH 3.7 adjusted with glacial acetic acid). The mobil phase is delivered by a HPLC pump (ESA) at 0.55 ml/min. Electrochemical detection is accomplished using an amperometric detector (Antec) with a glassy carbon electrode (0.8 V an Ag/AgCl reference) or a coloumetric detector (Choulochem II model ESA; with a high sensitivity analytical cell (5011). (0.4V an Ag/AgCl reference). Chromatograms are recorded by an integrator. The data are calculated as percent change of the basal concentration, the 100% value being defined as the average of the last 3 pretreatment values for each rat. The mean percentage values are then calculated for each 20 min sample for the rats in each group of treatment.

Method 12

Effect of a Compound on Turning Behaviour after 6-OHDA Lesion

In this test, the ability of a compound to influence the turning behaviour after a striatal or medial forebrain bundle and ventral tegmental area 6-OHDA lesion is assessed.

6-OHDA (20 μg free base dissolved in 0.9% NaCl supplemented with 0.02% ascorbic acid) is injected unilaterally in the striatum or in the medial forebrain bundle and the ventral tegmental area of halothane anaesthetised female Sprague Dawley rats weighing approximately 200-250 g with a glass capillary. Test compound or vehicle is administered i.p., p.o., s.c. or i.v. either daily or at specified time points starting after the 6-OHDA injection. The rotational behaviour of the 6-OHDA lesioned animals is monitored in automated rotometer bowls after administration of test compound alone or after administration of amphetamine (2.5 mg/kg i.p.), apomorphine (0.25 mg/kg s.c.), or L-dopa (2-10 mg/kg i.p.).

EXAMPLES

Example 1

Protection of the Substantia Nigra after Transient Global Ischaemia in Gerbils

Global forebrain ischemia was induced in Mongolian gerbils as described in test method 7 by occluding the common carotid arteries bilaterally for 10 min. The experiment was carried out for the following three groups of animals: 1) a control group (6 animals), 2) a group of animals subjected to carotid artery occlusion ischemia (6 animals) and 3) a group subjected to carotid artery occlusion ischemia and treatment with the test compound (8 animals). The animals of the control group were subjected to the same surgical procedure as group 2) except for the occlusion. The following test compound was used: (1R,2R,3S)-3-(3,4-dichlorophenyl)-tropane-2-O-methyl-aldoxime. The test compound was dosed 2 minutes after end of carotid artery occlusion at a concentration of 2 mg/kg i.p.

After 14 days, the animals were sacrificed and the brains sectioned. Sections comprising the substantia nigra were TH immunostained. The total number of TH positive cells after ischemia or in control animals were determined by means of stereological cell counting.

The results are shown in Table 1. In animals subjected to ischemia, the total number of TH positive cells in the substantia nigra (7510+/−1185) appeared to be lower than that in control animals (9531+/−653) indicating ischemia induced cell death in the substantia nigra. Surprisingly, the number of surviving TH positive cells in the substantia nigra after ischemia was apparently increased by treatment with the test compound indicating that this compound has a protective effect in ischemia.

| Group | Mean number of cells | SEM (number of cells) |
| --- | --- | --- |
| Control | 9531 | 653 |
| Ischemia | 7510 | 1185 |
| Ischemia + test compound | 10615 | 1403 |

The invention claimed is:

1. A method for the inhibiting dopamine reuptake associated with reduced blood flow to the brain or with an instance of a temporary break in blood supply to the brain in a subject, comprising administering to said subject a therapeutically effective amount of a tropane compound having dopamine reuptake inhibitor activity or a pharmaceutically acceptable salt thereof, wherein the tropane compound is a compound of the general formula (I)

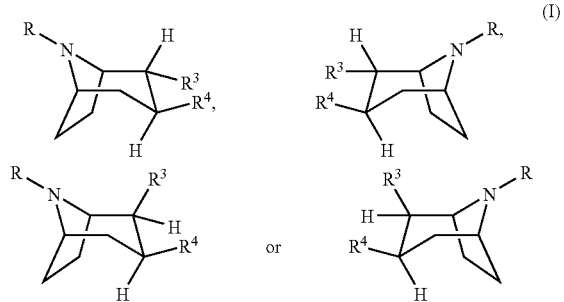

or a pharmaceutically acceptable addition salt thereof or the N-oxide thereof, wherein:

R is hydrogen, alkyl, alkenyl, alkynyl, cycloalkyl, cycloalkylalkyl or 2-hydroxyethyl;

$R^3$ is $CH_2$—X—R' wherein X is O or S and R' is methyl, ethyl, propyl, or cyclopropylmethyl, or $R^3$ is CH=NOR' wherein R' is hydrogen or alkyl, or $R^3$ is 1,2,4-oxadiazol-5-yl which may be substituted in the 3 position with alkyl; and $R^4$ is 3,4-methylenedioxyphenyl or $R^4$ is phenyl, benzyl, naphthyl, or heteroaryl all of which may be substituted one or more times with substituents selected from the group consisting of halogen, $CF_3$, CN, alkoxy, cycloalkoxy, alkyl, cycloalkyl, alkenyl, alkynyl, amino, nitro, and heteroaryl.

2. The method according to claim 1, wherein the tropane compound having dopamine reuptake inhibitor activity is selected from (1R,2R,3S)-2-(3-Cyclopropyl-1,2,4-oxadiazol-5-yl)-3-(4-fluorophenyl)tropane;

(1R,2R,3S)-3-(3,4-Dichlorophenyl)tropane-2-aldoxime;

(1R,2R,3S)-3-(3,4-Dichlorophenyl)-tropane-2-O-methyl-aldoxime;

(1R,2R,3S)-N-Normethyl-3-(3,4-dichlorophenyl)tropane-2-O-methyl-aldoxime;

(1R,2R,3S)-3-(4-Methylphenyl)tropane-2-O-methyl-aldoxime;

(1R,2R,3S)-3-(3,4-Dichlorophenyl)tropane-2-O-(1,1-dimethylethyl)-aldoxime;

(1R,2R,3S)-3-(4-Chlorophenyl)tropane-2-O-aldoxime;

(1R,2R,3S)-3-(4-Chlorophenyl)tropane-2-O-methylaldoxime;

(1R,2R,3S)-3-(3,4-Dichlorophenyl)tropane-2-O-(2-methylpropyl)-aldoxime;

(1R,2R,3S)-3-(3,4-Dichlorophenyl)tropane-2-O-cyclopropylmethyl-aldoxime;

(1R,2R,3S)-3-(3,4-Dichlorophenyl)tropane-2-O-ethyl-aldoxime;

(1R,2R,3S)-2-Methoxymethyl-3-(3,4-dichlorophenyl)-tropane;

(1R,2R,3S)-2-Isopropoxymethyl-3-(3,4-dichlorophenyl)-tropane;

(1R,2R,3S)-2-Ethoxymethyl-3-(3,4-dichlorophenyl)-tropane;

(1R,2R,3S)-2-Cyclopropylmethyloxymethyl-3-(3,4-dichlorophenyl)-tropane;

(1R,2R,3S)-2-Methoxymethyl-3-(4-chlorophenyl)-tropane;

(1R,2R,3S)-N-Normethyl-2-methoxymethyl-3-(4-chlorophenyl)-tropane;

(1R,2R,3S)-2-Ethoxymethyl-3-(4-chlorophenyl)-tropane;

(1R,2R,3S)-N-Normethyl-2-methoxymethyl-3-(3,4-dichlorophenyl)-tropane;

(1R,2R,3S)-N-Normethyl-2-ethoxymethyl-3-(3,4-dichlorophenyl)-tropane;

(1R,2R,3S)-N-Normethyl-2-ethoxymethyl-3-(4-chlorophenyl)-tropane;

(1R,2R,3S)-N-Normethyl-2-cyclopropylmethyloxymethyl-3-(4-chlorophenyl)-tropane;

(1R,2R,3S)-2-Cyclopropylmethyloxymethyl-3-(4-chlorophenyl)-tropane;

(1R,2R,3S)-2-Ethylthiomethyl-3-(3,4-dichlorophenyl)-tropane;

or a pharmaceutically acceptable addition salt thereof.

3. The method according to claim 1, wherein a disease to be treated is an ischemic disease, an anoxic episode, or an injury to the brain and other parts of the CNS caused by trauma or other injury.

4. The method according to claim 1, wherein the disease to be treated is selected from cerebrovascular disorder, cerebral ischemia or cerebral infarction resulting from thromboembolic or haemorrhagic stroke, cerebral vasospasm, hypoglycaemia, cardiac arrest, perinatal asphyxia, anoxia, anoxia resulting from near-drowning, pulmonary surgery or cerebral trauma.

5. The method according to claim 1, wherein a disease to be treated is selected from brain damage following or caused by: cerebral ischemia, cardiac arrest, cardiac surgery, stroke, neonatal hypoxia, hypoxia caused by compromised lung function, neonatal anoxia, anoxia caused by compromised lung function, cerebral trauma, secondary regional ischemia induced by brain oedema, increased intercranial pressure, open brain surgery, endarterectomy, surgical interventions involving temporary, artificially sustained arrest of cardiopulmonary functions resulting in impairment of cerebral blood flow, or emergency treatment involving cardiopulmonary resuscitation (CPR).

6. A method for the treatment of cerebral ischemia in a subject, comprising administering to said subject a therapeutically effective amount of a tropane compound having dopamine reuptake inhibitor activity or a pharmaceutically acceptable salt thereof, wherein the tropane compound having dopamine reuptake inhibitor activity is a compound of the general formula (I)

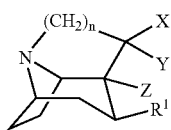

(II)

or a pharmaceutically acceptable addition salt thereof or the N-oxide thereof, wherein:
R is hydrogen, alkyl, alkenyl, alkynyl, cycloalkyl, cycloalkylalkyl or 2-hydroxyethyl;
$R^3$ is $CH_2$—X—R' wherein X is O or S and R' is methyl, ethyl, propyl, or cyclopropylmethyl, or $R^3$ is CH=NOR' wherein R' is hydrogen or alkyl, or $R^3$ is 1,2,4-oxadiazol-5-yl which may be substituted in the 3 position with alkyl; and
$R^4$ is 3,4-methylenedioxyphenyl or $R^4$ is phenyl, benzyl, naphthyl, or heteroaryl all of which may be substituted one or more times with substituents selected from the group consisting of halogen, $CF_3$, CN, alkoxy, cycloalkoxy, alkyl, cycloalkyl, alkenyl, alkynyl, amino, nitro, and heteroaryl.

7. The method according to claim 6, wherein the tropane compound having dopamine reuptake inhibitor activity is selected from
(1R,2R,3S)-2-(3-Cyclopropyl-1,2,4-oxadiazol-5-yl)-3-(4-fluorophenyl)tropane;
(1R,2R,3S)-3-(3,4-Dichlorophenyl)tropane-2-aldoxime;
(1R,2R,3S)-3-(3,4-Dichlorophenyl)-tropane-2-O-methyl-aldoxime;
(1R,2R,3S)-N-Normethyl-3-(3,4-dichlorophenyl)tropane-2-O-methyl-aldoxime;
(1R,2R,3S)-3-(4-Methylphenyl)tropane-2-O-methyl-aldoxime;
(1R,2R,3S)-3-(3,4-Dichlorophenyl)tropane-2-O-(1,1-dimethylethyl)-aldoxime;
(1R,2R,3S)-3-(4-Chlorophenyl)tropane-2-O-aldoxime;
(1R,2R,3S)-3-(4-Chlorophenyl)tropane-2-O-methylaldoxime;
(1R,2R,3S)-3-(3,4-Dichlorophenyl)tropane-2-O-(2-methylpropyl)-aldoxime;
(1R,2R,3S)-3-(3,4-Dichlorophenyl)tropane-2-O-cyclopropylmethyl-aldoxime;
(1R,2R,3S)-3-(3,4-Dichlorophenyl)tropane-2-O-ethyl-aldoxime;
(1R,2R,3S)-2-Methoxymethyl-3-(3,4-dichlorophenyl)-tropane;
(1R,2R,3S)-2-Isopropoxymethyl-3-(3,4-dichlorophenyl)-tropane;
(1R,2R,3S)-2-Ethoxymethyl-3-(3,4-dichlorophenyl)-tropane;
(1R,2R,3S)-2-Cyclopropylmethyloxymethyl-3-(3,4-dichlorophenyl)-tropane;
(1R,2R,3S)-2-Methoxymethyl-3-(4-chlorophenyl)-tropane;
(1R,2R,3S)-N-Normethyl-2-methoxymethyl-3-(4-chlorophenyl)-tropane;
(1R,2R,3S)-2-Ethoxymethyl-3-(4-chlorophenyl)-tropane;
(1R,2R,3S)-N-Normethyl-2-methoxymethyl-3-(3,4-dichlorophenyl)-tropane;
(1R,2R,3S)-N-Normethyl-2-ethoxymethyl-3-(3,4-dichlorophenyl)-tropane;
(1R,2R,3S)-N-Normethyl-2-ethoxymethyl-3-(4-chlorophenyl)-tropane;
(1R,2R,3S)-N-Normethyl-2-cyclopropylmethyloxymethyl-3-(4-chlorophenyl)-tropane;
(1R,2R,3S)-2-Cyclopropylmethyloxymethyl-3-(4-chlorophenyl)-tropane;
(1R,2R,3S)-2-Ethylthiomethyl-3-(3,4-dichlorophenyl)-tropane;

or a pharmaceutically acceptable addition salt thereof.

8. The method according to claim 6, wherein the tropane compound having dopamine reuptake inhibitor activity is (1R,2R,3S)-3-(3,4-dichlorophenyl)-tropane-2-O-methyl-aldoxime.

* * * * *